United States Patent [19]

Boone, Sr.

[11] 4,332,245

[45] Jun. 1, 1982

[54] EMERGENCY TRACHEA AIRWAY

[76] Inventor: Frank J. Boone, Sr., 312 N. 12th St., Murray, Ky. 42071

[21] Appl. No.: 179,931

[22] Filed: Aug. 19, 1980

[51] Int. Cl.³ .................... A61M 25/02; A61M 25/00
[52] U.S. Cl. ............................ 128/207.17; 128/207.14
[58] Field of Search ...................... 128/207.14, 207.15, 128/207.16, 207.17, 200.26, 349 R, 347, 10

[56] References Cited

U.S. PATENT DOCUMENTS

| 2,269,823 | 1/1942 | Kreiselman | 128/207.15 |
| 3,175,557 | 3/1965 | Hammond | 128/207.14 |
| 3,973,569 | 8/1976 | Sheridan et al. | 128/207.15 |

FOREIGN PATENT DOCUMENTS

| 649230 | 1/1951 | United Kingdom | 128/207.14 |
| 1174397 | 12/1969 | United Kingdom | 128/207.14 |

OTHER PUBLICATIONS

Frey, "A New Endotracheal Catheter Fixation", Brit. J. Anaesth. (1955), 27,260.

Primary Examiner—Henry J. Recla
Attorney, Agent, or Firm—Harvey B. Jacobson

[57] ABSTRACT

An elongated, inverted and generally L-shaped tubular body is provided including generally right angularly disposed horizontal and vertical tube sections intersecting at one pair of ends thereof. The lower end of the vertical tube section includes a diametrically reduced terminal end beveled toward the upper end of the vertical tube section on the side thereof remote from the vertical tube section side from which the horizontal tube section projects and the horizontal tube section includes an enlarged abutment flange thereon intermediate the opposite ends thereof. The side of the diametrically reduced terminal end toward which the latter is beveled is coextensive with the corresponding side of the upper end of the vertical tube section and the remote side of the terminal end portion is inwardly offset from the corresponding side of the upper end of the vertical tube section, the wall portion of the L-shaped tubular body connecting the inwardly offset side of the terminal end portion and the corresponding side of the upper end of the vertical tube section being upwardly and outwardly inclined relative to the lower terminal end.

7 Claims, 5 Drawing Figures

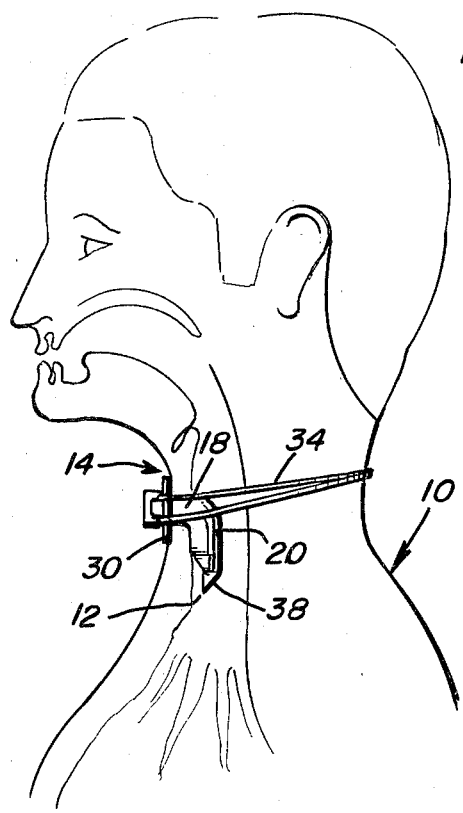
FIG. 1
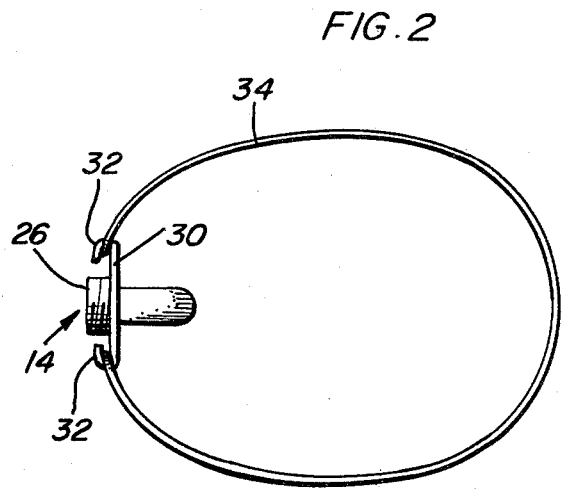
FIG. 2
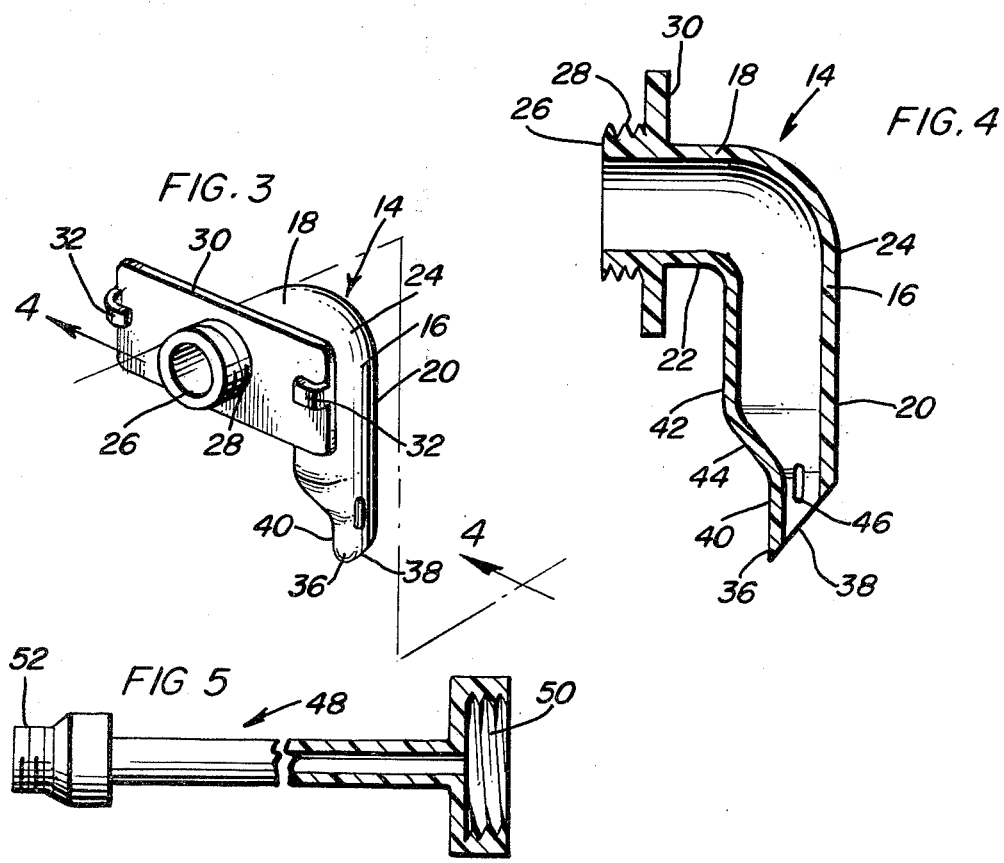
FIG. 3
FIG. 4
FIG. 5

EMERGENCY TRACHEA AIRWAY

BACKGROUND OF THE INVENTION

Various situations arise requiring the use of an emergency trachea airway in order to save a person's life.

Heretofore various forms of emergency trachea airways and other devices have been provided including some of the general structural and operational features of the instant invention. Examples of these previously known devices are disclosed in U.S. Pat. Nos. 460,987, 2,865,374, 3,415,250, 3,476,113 and 3,538,918.

However, these previously known devices are not readily useable in emergency situations by only semi-skilled persons and in a manner preventing passage of fluent or bulk materials downwardly passed the emergency airways after they have been placed in position. Accordingly, a need exists for an improved form of emergency trachea airway.

BRIEF DESCRIPTION OF THE INVENTION

The emergency trachea airway of the instant invention is constructed in a manner enabling its proper placement by semi-skilled persons and includes structural features facilitating proper placement relative to a patient. Further, the emergency trachea airway also includes structural features which facilitate the blocking of the passage of fluent as well as bulk materials downwardly through an associated trachea past the emergency trachea airway subsequent to the latter being properly positioned in an associated trachea.

The main object of this invention is to provide an improved emergency trachea airway constructed in a manner to facilitate proper insertion of the airway, even by semi-skilled persons.

Another object of this invention is to provide an emergency trachea airway constructed in a manner enabling it to be readily operatively associated with a force breathing apparatus.

A further important object of this invention is to provide an emergency trachea airway including structure facilitating the retention of the airway in proper position during transport of an associated patient from an accident scene to a hospital.

Yet another important object of this invention is to provide an emergency trachea airway in accordance with the preceding objects and constructed in a manner to facilitate the blockage of fluent as well as bulk material downwardly through an associated trachea passed the emergency airway subsequent to the emergency airway being properly positioned in the trachea.

A final object of this invention to be specifically enumerated herein is to provide an emergency trachea airway constructed in accordance with the preceding objects and which will conform to conventional forms of manufacture, be of simple construction and easy to use so as to provide a device that will be economically feasible, long lasting and relatively trouble-free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is an elevational view of the emergency trachea airway of the instant invention shown in operative position relative to a patient and secured in operative position against shifting therefrom;

FIG. 2 is a top plan view of the assemblage illustrated in FIG. 1;

FIG. 3 is a perspective view of the emergency trachea airway;

FIG. 4 is an enlarged vertical sectional view taken substantially upon the plane indicated by the section line 4—4 of FIG. 3; and FIG. 5 is a fragmentary longitudinal sectional view of a flexible tube removably engageable with the airway and operable to connect breathing assist apparatus to the airway.

DETAILED DESCRIPTION OF THE INVENTION

Referring now more specifically to the drawings, the numeral 10 generally designates a patient including a trachea zone 12 into which the emergency trachea airway of the instant invention has been inserted. The emergency trachea airway is generally referred to by the reference numeral 14 and includes a tubular body 16 consisting of an upper horizontal tube section or portion 18 and a lower vertical tube portion or section 20. The upper tube portion 18 includes a rear end 22 which intersects with and opens into the upper end 24 of the tube portion 20 and a forward end 26 which is externally threaded as at 28. In addition, the tube portion 18 includes an enlarged horizontally elongated abutment flange 30 intermediate its opposite ends and closely adjacent the forward end 26. The four corner portions of flange 30 are rounded and the front surface of the abutment flange 30 includes opposite end J-shaped clips 32 which open toward each other and with which opposite looped ends of a neck encircling airway retention member 34 are engaged. The retention member 34 illustrated is in the form of an endless elastic member, but may be in the form of a simple tie member.

The rear end 22 of the tubular portion 18 curves smoothly downwardly into the upper end 24 of the tubular portion 20 and the lower end 36 of the tubular portion 20 is diametrically reduced and rearwardly and upwardly beveled as at 38. The rear wall of the diametrically reduced terminal end 36 is co-extensive with the rear wall of the upper end portion 24, but the front wall 40 of the terminal end 36 is rearwardly offset relative to the front wall 42 of the upper end portion 24. Further, the tubular body 16 includes a forwardly and upwardly inclined forward wall portion 44 interconnecting the rearwardly offset forward wall portion 40 of the terminal end 36 and the front wall 42 of the upper end 24. The inclined wall portion 44 defines and inclined shoulder to offer resistance against further insertion of the terminal end 36 into the trachea zone 12 and a shoulder about which the emergency trachea airway 14 may be pivoted to upwardly swing the tube portion 18 after the terminal end 36 has been initially inserted into the trachea zone 12 and prior to subsequent downward displacement of the upper end 24 into the trachea zone 12, to thus facilitate proper insertion of the emergency trachea airway 14 by even unskilled persons. The terminal end 36 includes opposite side supplemental air openings 46 formed therein as back-up openings in the event the central lower portion of the terminal end 36 should become blocked.

After the emergency trachea airway terminal end 36 has been initially inserted into the trachea zone 12 and the tube portion 18 has been swung upwardly while maintaining downward pressure on the emergency trachea airway 14, the airway 14 will be positioned for further insertion of the tube portion 20 downwardly into the trachea zone 12. When the larger diameter upper end portion 24 of the tube portion 20 is properly downwardly inserted into the trachea zone 12, the upper end 24 occupies substantially the entire internal cross-sectional area of the trachea zone 12 and thus prevents downward movement of fluent as well as bulk materials through the trachea zone 12 past the emergency trachea airway 14.

The tube assembly illustrated in FIG. 5 is referred to in general by the reference numeral 48 and includes an internally threaded coupling end 50 for removable threaded engagement with the threads 28. The remote end of the tube assembly 48 is of a configuration as at 52 for ready removable connection with a mechanical breathing assist apparatus (not shown). The tube assembly 48 is flexible although sufficiently stiff to retain its tubular shape.

After the emergency trachea airway has been properly inserted, the airway retention member 34 may be properly engaged with the lug 32 in the manner illustrated in FIGS. 1 and 2 of the drawings in order that the airway 14 will be retained in proper position.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. An emergency trachea airway, said airway including an inverted generally L-shaped tubular body including generally right angularly disposed tube sections intersecting at one pair of ends thereof, a first end of one tube section remote from the other tube section including a beveled diametrically reduced terminal end beveled toward the first end and to the side of the one tube section opposite the side thereof from which the other tube section projects, said other tube section including an enlarged abutment flange thereon intermediate said one tube section and the free end of the other tube section, said diametrically reduced terminal end being eccentrically positioned relative to the longitudinal center line of the second end of said one tube section toward the side of said second end of said one tube section remote from the side of said one tube section from which the other tube section projects, the side of said diametrically reduced terminal end corresponding to the side of the second end of the one tube section from which the other tube section projects being inwardly offset from the corresponding side of the second end of said one tube section, the wall portion of said tubular body connecting the inwardly offset side of the terminal end with the corresponding side of said second end of said one tube section being outwardly inclined from said inwardly offset side toward said other tube section.

2. An emergency trachea airway, said airway including an inverted generally L-shaped tubular body including generally right angularly disposed tube sections intersecting at one pair of ends thereof, a first end of one tube section remote from the other tube section including a beveled diametrically reduced terminal end beveled toward the first end and to the side of the one tube section opposite the side thereof from which the other tube section projects, said other tube section including an enlarged abutment flange thereon intermediate said one tube section and the free end of the other tube section, the side of said diametrically reduced terminal end remote from the side of the one tube section from which the other tube section projects being substantially co-extensive with the corresponding side of the second end of said one tube section, the side of said diametrically reduced terminal end corresponding to the side of the second end of the one tube section from which the other tube section projects being inwardly offset from the corresponding side of the second end of said one tube section, the wall portion of said tubular body connecting the inwardly offset side of the terminal end with the corresponding side of said second end of said one tube section being outwardly inclined from said inwardly offset side toward said other tube section.

3. The airway of claim 2 wherein said enlarged abutment flange includes opposite side portions disposed on opposite sides of a plane containing said L-shaped tubular body, said opposite side portions including anchor portions, and an elongated flexible airway positioning member having its opposite ends anchored relative to said anchor portions, said elongated member being adapted to encircle the neck of a patient in which the airway has been inserted.

4. The airway of claim 2 wherein the free end of said other tube section remote from said one tube section is externally threaded, an elongated flexible tube section, one end of said flexible tube section being internally threaded for removable threaded engagement with the externally threaded end of said free end of said one tube section, the other end of said elongated flexible tube section being adapted for removable coupling to a mechanical breathing assist apparatus.

5. An emergency trachea airway, said airway including an inverted generally L-shaped tubular body including generally right angularly disposed tube sections intersecting at one pair of ends thereof, a first end of one tube section remote from the other tube section including a beveled diametrically reduced terminal end beveled toward the first end and to the side of the one tube section opposite the side thereof from which the other tube section projects, said other tube section including an enlarged abutment flange thereon intermediate said one tube section and the free end of the other tube section, the free end of said other tube section remote from said one tube section being externally threaded, an elongated flexible tube section, one end of said flexible tube section being internally threaded for removable threaded engagement with the externally threaded end of said free end of said one tube section, the other end of said elongated flexible tube section being adapted for removable coupling to a mechanical breathing assist apparatus, said enlarged abutment flange including opposite side portions disposed on opposite sides of a plane containing said L-shaped tubular body, said opposite side portions including anchor portions, and an elongated flexible airway positioning member having its opposite ends anchored relative to said anchor portions, said elongated member being adapted to encircle the neck of a patient in which the airway has been inserted, the side of said diametrically reduced terminal end remote from the side of the one tube section from which the other tube section projects being substantially co-extensive with the corresponding side of the second end of said one tube section, the side of said diametrically reduced terminal end corresponding to the side of the second end of the one tube section from which the other tube section projects being inwardly offset from the corresponding side of the second end of one tube section, the wall portion of said tubular body connecting the inwardly offset side of the terminal end with the corresponding side of said second end of said one tube section being outwardly inclined from said inwardly offset side toward said other tube section.

6. An emergency trachea airway, said airway including an inverted L-shaped tubular body including generally right angularly disposed upper horizontal and lower vertical tube sections intersecting at a first end of said horizontal tube section and the upper end of said vertical tube section, the lower end of said vertical tube section including a beveled diametrically reduced terminal end inclined toward said upper end and to the side of said vertical tube section opposite to the side thereof from which the horizontal tube section projects, the side of said diametrically reduced terminal end remote from the side of said vertical tube section from which the horizontal tube section projects being substantially co-extensive with the corresponding side of the upper end of said vertical tube section, the side of said diametrically reduced terminal end corresponding to the side of said vertical tube section from which said horizontal tube section projects being inwardly offset from the corresponding side of the upper end of said vertical tube section, the wall portion of said vertical tube section connecting the inwardly offset side of said terminal end with the corresponding side of the upper end of said vertical tube section being upwardly and outwardly inclined.

7. The airway of claim 6 wherein the outer end of said horizontal tube section remote from said vertical tube section is externally threaded, an elongated flexible tube member, one end of said tube member being internally threaded for removable threaded engagement with the externally threaded end of said horizontal tube section, the other end of said tube member being adapted for releasable connection with a mechanical breathing assist apparatus.

* * * * *